United States Patent [19]

Munson, Jr. et al.

[11] Patent Number: 4,604,404

[45] Date of Patent: Aug. 5, 1986

[54] ANTIVIRAL SULFONATED NAPHTHALENE FORMALDEHYDE CONDENSATION POLYMERS

[75] Inventors: Harry R. Munson, Jr.; Robert W. Tankersley, Jr., both of Richmond, Va.

[73] Assignee: A. H. Robins Company, Inc., Richmond, Va.

[21] Appl. No.: 719,296

[22] Filed: Apr. 3, 1985

[51] Int. Cl.$^4$ .................. A61K 31/255; A61K 31/315
[52] U.S. Cl. .................................... 514/494; 514/517; 514/518

[58] Field of Search ....................... 514/494, 517, 518

[56] References Cited

PUBLICATIONS

Chem. Abst., vol. 75 (1971) 72945h.

Primary Examiner—Stanley J. Friedman

[57] ABSTRACT

A method is disclosed for combating *Herpes simplex* viruses, Types I and II, which comprises topically applying and antiviral arylsulfonic acid polymer to the animal tissue under attack. Bacterial infections are also affectively treated.

5 Claims, No Drawings

ANTIVIRAL SULFONATED NAPHTHALENE FORMALDEHYDE CONDENSATION POLYMERS

BACKGROUND OF THE INVENTION

1. Field of the Invention

The present invention is concerned with the use of condensation polymers of formaldehyde and arylsulfonic acids as antiviral agents and, in particular, the use of condensation polymers of formaldehyde and naphthalenesulfonic acids to protect humans and other warm-blooded animals from infection by enveloped viruses, e.g., the influenza group of viruses, the herpes viruses, and from infection by other microorganisms causing venereal disease in humans.

2. Description of the Prior Art

Usually Herpes simplex viral infections are mild, acute or recurrent episodes with topical lesion resulting which causes pair and temporary cosmetic disfigurement during which time the host is potentially infectious to others. More rarely, the infection takes the form of a serious corneal, encephalitic or systemic disease. Type I Herpes simplex viral infections generally are associated with the oral cavity and Type II Herpes simplex viruses generally occur in the genitourinary tract of both sexes in humans; however, there is some crossover of infection.

No specific anti-herpes agents are available for use in a host having the usual mild, acute or recurrent episode despite the obvious need for such agents. A wide range of non-specific treatments have some palliative and antiseptic effect such as alum, vinegar, ether, camphor and mixed culture of Lactobacillus acidophilus and L. bulgaricus with naturally occurring metabolic products produced by these organisms.

For more serious corneal, encephalitic and systemic infections, three specific anti-herpes agents are available: 5-iodo-2-deoxyuridine, acyclovir and 9-D-arabinofuranosyladenine. However, because the mechanism of control of virus with these agents involves interference with DNA synthesis, potential side effects detrimental to other DNA syntheses vital to the host also occurs.

Another approach to the therapy of Herpes simplex viral infections has been the use of photo-inactivating dyes. This procedure requires that the surface of the lesion be broken, the underlying infected tissue painted with a dye such as neutral red or proflavine and the painted area exposed to visible light of sufficient intensity to inactivate the stained virus. The efficacy and safety of the procedure using photoinactivating dyes have not been established and special equipment and trained personnel are required to administer the treatment.

U.S. Pat. No. 4,185,097, assigned to A. H. Robins Company discloses a method for combating Herpes simplex viruses, Type I and II, by topically applying an antiviral lignosulfonate to the animal tissue under attack.

Monomeric and polymeric sulfonates have been found to possess additional medicinal usefulness: U.S. Pat. Nos. 4,361,547 and 4,364,927 disclose compositions and methods for preventing the attachment of dental plaque to the surfaces of the teeth of mammals comprising certain sulfonated aromatic formaldehyde condensation polymers and the pharmaceutically acceptable salts thereof in a pharmaceutically acceptable vehicle, and the periodic application thereof to teeth.

U.S. Pat. No. 4,375,461 discloses compositions and methods for preventing the attachment of dental plaque to the surfaces of the teeth of mammals comprising certain sulfonated vinylaromatic homopolymers and copolymers and the pharmaceutically acceptable salts thereof in a pharmaceutically acceptable vehicle, and the periodic application thereof to teeth.

Similarly, U.S. Pat. No. 4,362,712 discloses polymers useful in compositions and methods for preventing the attachment of dental plaque to the surface of the teeth of mammals comprising alkali metal salts of certain carboxylated naphthalene formaldehyde polymers.

Aromatic virucides such as sodium (1-methylundecyl) benzenesulfonate have been described as showing virucidal activity against tobacco mosaic virus. Other non-polymeric aromatic sulfonic acids have been disclosed as viral inhibitors, although, none of such materials have been disclosed as providing protection against Herpes simplex virus infection in animals.

Topical compositions for treating Herpes infections and containing sulfonated polysaccharides have been described. These polymeric materials are not aromatic sulfonic acids and are distinctly different from formaldehyde-aromatic sulfonic acid condensation polymers.

SUMMARY OF THE INVENTION

The present invention is based on the discovery that topical application of an antiviral arylsulfonic acid polymer to the affected area of a host mammal infected with Type I or Type II Herpes simplex viruses controls the virus and reduces the extent of infection. The method may also be used to combat infection prior to exposure. The preferred arylsulfonic acid polymers are polymeric sulfonates formed by the condensation of formaldehyde with an aromatic sulfonic acid as more fully described below. The arylsulfonic acid polymers may be in the free acid form or in the form of pharmaceutically acceptable salts such as sodium and zinc. The polymers can be separated from low molecular weight materials and inorganic salts by using ultrafiltration methods. The combination of cation exchange and ultrafiltration can be used to prepare and purify other salt forms.

DETAILED DESCRIPTION OF THE INVENTION

The preparation of formaldehyde condensation polymers of aromatic sulfonic acids is well known and disclosed in the patent literature. For example, U.S. Pat. Nos. 4,364,927; 4,361,157; 3,067,243; 3,277,162; and German Pat. Nos. 1,137,005 and 1,157,214 disclose the preparation of formaldehyde condensation polymers of aromatic sulfonic acids. Moreover, formaldehyde condensed naphthalene sulfonates of the Lomar TM, Tamol TM, Daxad TM, and Darvan TM types have been used in emulsion polymerization as secondary emulsifiers. U.S. Pat. No. 4,258,871 also discloses methods of preparing formaldehydenaphthalene sulfonic acid condensation polymers. All of the above references are herein incorporated by reference. Other methods of preparation are disclosed below.

The polymeric arylsulfonates found useful as antiviral agents and, in particular, which show antiviral activity against Herpes viruses are essentially sulfonated derivatives of formaldehyde condensation polymers of certain aromatic compounds wherein the repeating unit of the polymer is selected from the group consisting of structures A, B, C, D and E described below.

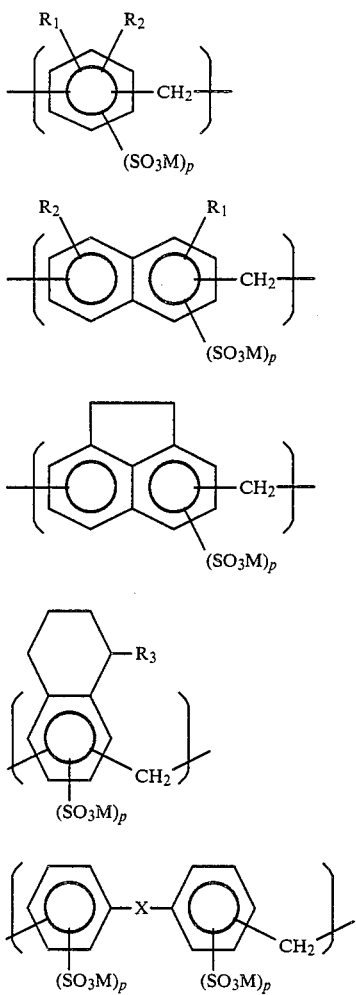

wherein $R_1$ and $R_2$ are each independently selected from the group consisting of hydrogen, linear or branched alkyl of up to 20 carbon atoms, alkoxy of 1–20 carbon atoms, fluorine, chlorine, and bromine; $R_3$ is hydrogen or an alkoxy group of up to 20 carbons, X is a linkage selected from the group consisting of a direct covalent bond between the aromatic rings, a lower alkylene of 1 to 5 carbon atoms, a lower alkylidene having 2 to 5 carbon atoms, oxygen, sulfur, and $O(CH_2)_nO$, where n is an integer from 2 to 20; p is from about 0.4 to about 1.2, (preferably about 1), the sum of q and r is between about 0.8 and about 2.4 (preferably from about 1 to about 2); and M is selected from the group consisting of lithium, sodium, potassium, calcium, magnesium, zinc, aluminum, hydrogen, ammonium and substituted ammonium ions derived from pharmaceutically acceptable organic amines. The sodium and zinc salts are particualarly preferred. In general, the method and ammonium salts are preferred over the free sulfonic acid derivatives because of their higher water solubility and lower degree of acidity (closer to neutrality).

The formaldehyde polymers that can be sulfonated to form antiviral agents useful in this invention are preferably prepared by the acid catalyzed condensation of aqueous 37% formaldehyde or paraformaldehyde with selected aromatic compounds under standard conditions reported in the literature and reviewed extensively in the text by J. F. Walker, "Formaldehyde", R. E. Krieger Publishing Co., Third Edition, 1975. By selecting aromatic compounds of varied structure, condensation reactions with aromatic compounds of varied structure, condensation reactions with formaldehyde can afford a wide variety of aromatic/formaldehyde polymers, having generalized structure (I), wherein the unsulfonated aromatic moiety, Ar, corresponds to the aromatic structures in the repeating units of structures (A) through (E) of the sulfonated polymers defined above.

Typical examples of aromatic compounds which can be utilized for preparation of the formaldehyde polymers of general structure (I) are toluene, xylene, ethylbenzene, propylbenzene, isopropylbenzene, butylbenzene, tertiary-butylbenzene, octylbenzene, nonylbenzene, dodecylbenzene, octadecylbenzene, anisole, m-chloroanisole, diphenyl, diphenylmethane, 2,2-diphenylpropane, 1,2-diphenyl ethane(bibenzyl), 1,5-diphenylpentane, diphenyl ether, diphenyl sulfide, 2,6-dimethylnaphthalene, nonylnaphthalene, 1-chloronaphthalene; 1,2,3,4-tetrahydronaphthalene (tetralin); 1-methoxy-1,2,3,4-tetrahydronaphthalene, 1-dodecyloxy-1,2,3,4-tetrahydronaphthalene; acenaphthalene; 1,2-bis(phenoxy)ethane; 1,6-bis(phenoxy)hexane; and 1,12-bis(phenoxy)dodecane.

As indicated in structures A-E, the exact position or orientation of the methylene ($-CH_2-$) linkages on the aromatic rings is not known and is generally recognized as being complex and varied. It is well understood that some of the formaldehyde linkages may not be solely of the $-CH_2-$ type but can also involve some extended units, such as $CH_2OCH_2$ and $CH_2(OCH_2)_nOCH_2$, or other possiblities (cf. Walker, supra). However, despite these uncertainties, NMR data on the unsulfonated precursors as well as the sulfonated formaldehyde polymers of this invention indicated that the formaldehyde linkages consist essentially of the methylene linkage depicted in structures A–E. The molecular weights of the unsulfonated polymers will generally be in the 2000–5000 molecular weight range.

The formaldehyde polymers are prepared by heating approximately equimolar quantities of formaldehyde and the selected aromatic compound in an inert solvent, in the presence of an acid catalyst such as sufuric acid, p-toluenesulfonic acid, methanesulfonic acid, or perchloric acid, for several hours. Depending on the nature of the formaldehyde polymer, the latter precipitates from the reaction mixture either directly on cooling to room temperature or upon quenching in water. The preferred solvent for the reaction is acetic acid, a solvent known to favor formation of polymers having oxygen-free linkages (Walker, supra, p. 439), such as those represented by structure (I).

The sulfonated formaldehyde polymers of this invention have a molecular weight of about 500 to 10,000 preferably about 2,000 to 5,000. They are substantially soluble in water or mixed solvents comprising water and an organic solvent miscible therewith (generally at least 1% w/w). The degree of sulfonation (D.S.), as defined herein, is the average number of sulfonate or sulfonic acid groups per repeat unit of the polymeric structure.

Preferred sulfonation agents for preparing useful sulfonated polymeric antiviral agents of this invention are anhydrous sulfur trioxide, triethylphosphate (TEP) complexes of sulfur trioxide, and chlorosulfonic acid. Due to the high reactivity of sulfur trioxide and its potent dehydration properties, sulfonation reactions with sulfur trioxide sometimes result in formation of highly insoluble polymer dispersions due to crosslinking caused by inter-polymer chain sulfone formation. In these situations, it is found preferable to moderate the sulfonation reactivity by utilization of the sulfur trioxide complexes with triethyl phosphate (TEP), which minimize or essentially eliminate formation of crosslinked by-products [cf. A. F. Turbak, Ind. Eng. Chem., Prod. R & D, 1, 275(1962); U.S. Pat. No. 3,072,619 (Jan. 8, 1963); A. F. Turbak and A. Noshay, U.S. Pat. No. 3,206,492 (Sept. 14, 1965); N. H. Canter, U.S. Pat. No. 3,642,728 (Feb. 15, 1972); A. Noshay and L. M. Robeson, J. Applied Polymer Science, 20, 1885 (1976)]. In some instances where it is difficult to effect sulfonation under milder conditions with the complexes, sulfonation with sulfur trioxide (alone) or chlorosulfonic acid is more effective.

Sulfonations are effected in solvents such as methylene chloride, 1,2-dichloroethane, and chloroform, since these are generally good solvents for the starting aromatic polymer and poor solvents for the sulfonated polymer. In those instances where the product is soluble in the reaction medium and does not precipitate, the sulfonated polymer is isolated by removing the solvent and converted to well-defined solids by either trituration or slurrying with an appropriate non-solvent.

Temperature control of the sulfonation reaction with sulfur trioxide and its complexes with TEP is not very critical. Acceptable results are obtained over a temperature range of −20° C. to +40° C. range. Sulfonations are generally effected at ambient room temperatures, since the sulfonation exotherm is very mild and rarely results in temperature increases beyond 35° C.

Typical impurities in the sulfonated polymer are small amounts of unreacted polymer, excess sulfonation agent (as sulfuric acid), and residual triethyl phosphate which are occluded in the solid polymer. Substantial purification can be effected by slurrying the polymeric sulfonic acid derivatives in non-solvents therefor, such as the halocarbons. Removal of the free sulfuric acid is difficult, since it complexes strongly with the polymeric product. Diethyl ether is an exceptionally good complexing agent for sulfuric acid and effectively removed this contaminant when freshly isolated polymeric solids are slurried in the ether and filtered. Other effective additives for sulfuric acid removal are halocarbon solvent blends with diethyl ether and other oxygenated solvents, such as ethyl acetate and acetone. The sulfuric acid, if not removed, results in contamination of the metal salts with, e.g. sodium sulfate, in the case where the sodium sulfonate polymer is produced.

The preferred process for purification of the sulfonated polymers, particularly highly water soluble types, is by dialysis in membrane tubes or hollow fiber dialyzing units having a molecular weight cut-off well below the molecular weight of the polymer. Dialysis removes all of the low molecular impurities, triethyl phosphate, and inorganic salts. High purity polymers are isolated as solids by freeze-drying or spray drying the dialyzed polymer solution.

The D.S. of the sulfonated polymers can be varied by adjusting the molar ratio of sulfonating agent to polymer. In preparing the sulfonated polymers according to the above-described method, the exact position of sulfonation on the aromatic rings is not known with certainty, nor is it considered important in the practice of this invention. The D.S. of the formaldehyde polymers, either as their sulfonic acid or sulfonate salt derivatives, can be determined by any of several methods: (a) NMR analysis, (b) elemental analysis for sulfur to carbon ratio determination, (c) direct titration of the sulfonic acid derivative with standard sodium hydroxide to obtain the milliequivalents of sulfonic acid groups per gram of sample, a value approximately equivalent to the ion-exchange capacity of the sulfonated polymer, or (d) atomic absorption assay for the metal content of carefully purified samples of the sulfonated salts.

The alkali metal salts of the sulfonated polymers are conveniently prepared by neutralization of a water or alcohol solution of the polymeric sulfonic acid derivative with alkali metal hydroxide solutions to the potentiometric endpoint. The salts are recovered by filtration, solvent stripping, or freeze drying, depending on the type of solvent used and whether the salt precipitates directly from the solvent media. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly and are collected, or they are isolated after solvent stripping. Purification of the sulfonate salt by dialysis is the preferred procedure for the more highly water soluble salts.

Multivalent metal salts, such as calcium, magnesium, zinc, and aluminum salts, of the sulfonated polymers are prepared by methods similar to those described above.

The preferred polymeric arylsulfonates found useful as antiviral agents and, in particular, as having antiviral activities against Herpes viruses, are formaldehyde condensation polymers of naphthalene sulfonic acids. Generally, these are employed in the form of pharmaceutically acceptable salts wherein the cation is selected from the group consisting of lithium, sodium, potassium, calcium, magnesium, zinc, aluminum, hydrogen, ammonium and substituted ammonium ions derived from pharmaceutically acceptable organic amines. The sodium and zinc salts are particularly preferred. The formaldehyde condensation polymers of sulfonic acids which are preferred in the present invention are represented by structural formula (B).

The commercially available sulfonated polymers useful in this invention are understood to be prepared by condensation of formaldehyde with naphthalene sulfonic acid and therefore have a degree of sulfonation of essentially 1. However, the present invention is not restricted to the use of these commercially available polymers, but includes analogous formaldehyde-naphthalene condensation products wherein the degree of sulfonation is in the range of from about 0.4 to about 1.4.

Polymers useful in this invention may have a degree of sulfonation substantially different from 1 and can be prepared by sulfonation of naphthalene formaldehyde condensation polymer precursors such as discussed previously.

The arylsulfonic acid polymers of the present invention are administered topically to the tissue of the host under viral attack in liquid forms such as solutions, emulsions, and sprays; in solid and semi-solid forms such as suppositories, powders, jellies, ointments, creams, troches, pastilles, lozenges or any solids or semi-solids capable of releasing arylsulfonic acid polymers over a period of time. When the treatment is in the mouth, sprays, mouthwashes and swabs are particularly effective means of application. Suitable liquid preparations can be prepared wherein the concentration of the arylsulfonic acid polymers is 0.5 to 20.0 percent, the preferred concentration being 1.0 to 10.0 percent. The concentration of arylsulfonic acid polymers in the solid preparation can also be 0.5 to 20%, the preferred concentration being 3.0 to 10.0 percent.

The following examples illustrate the polymer which are useful in the method of this invention. It is to be understood that the examples are merely illustrative of which polymers can be used and are not to be construed as limiting.

VIROLOGY

Methods (1) Antiviral Test Procedures, Experimental Compounds vs. Viruses in Cell Culture The test system consists of monolayers of a continuous human cell line, the HEp-2 cell, infected with 30–100 plaque-forming units of *Herpes simplex* virus Type I or II and incubated for 72 hrs. at 35° C.

Experimental compounds are made up in tissue culture medium and applied to the cell monolayers immediately after infection at concentrations of one microgram to 1 mg. per monolayer. Activity is judged by comparing the number of plaques formed in the control monolayers with the number formed in each treated monolayer and expressing the results in percent plaque reduction. Active compounds are those that show 50% plaque reduction. Combinations of polymers were also tested for the purpose of determining whether synergistic antiviral activity could be detected.

(2) Antiviral Test Procedure, Experimental Compounds vs. Genital *Herpes Simplex* Virus (HSV) Infection in Animals.

Virgin female guinea pigs weighing 250 grams each constitute the test system. Animals are infected by mildly abrading the vaginal mucosa, e.g. with a dry cotton swab, and instilling HSV Type I or II into the vagina. The virus dose is adjusted to infect 80–100% of unprotected animals. Experimental compounds at various dose levels are administered as intravaginal douches at intervals before and after infection. Activity is evaluated in terms of infection and survival of treated animals as compared to untreated control animals.

EXAMPLE I (*Herpes Simplex*, Virus, Type 1, in Human Cell Line)

Antiviral activity of polymers in terms of 50% plaque reduction in HEp-2 monolayers infected with *Herpes simplex* virus Type I was determined by method (1) above. Results are in Table 1.

EXAMPLE 2

(*Herpes Simplex* Virus, Type II, in Human Cell Line).

Antiviral activity of polymers in terms of 50% plaque reduction in HEp-2 monolayers infected with *Herpes simplex* virus Type II was determined by method (1) above. Results are in Table 2.

EXAMPLE 3

(Synergism Studies in Cell Culture)

The synergistic action of active polymers in terms of 50% plaque reduction in HEp-2 monolayer infected with *Herpes simplex* virus was also determined, using combinations of polymers at concentrations below those shown to be active when the individual polymers were tested. Results are listed in Table 3.

EXAMPLE 4

(*Herpes Simplex* Virus—Guinea Pigs)

Antiviral activity, in terms of mean survival days and percentages of guinea pigs protected against vaginal infection with *Herpes simplex* virus, was determined by method (2) above, topically applying polymer periodically as douches, pre and post infection. Results of tests using single compounds are shown in Table 4; test results using combinations of compounds are shown in table 5.

BACTERIOLOGY

Methods (1) Experimental compounds tested vs *Neisseria gonorrhoeae.*

The test system consists of petri dishes containing chocolate agar, inoculated with a saline suspension of *N. gonorrhoeae* harvested from a 48 hr. culture on chocolate agar. The bacterial suspension is spread evenly over the agar and allowed to dry at room temp. Test compounds are dissolved at a 5% concentration, w/v, in pH 7.0 phosphate buffer, ¼ in. filter paper discs are dipped into the solutions and let to air dry. Discs dipped in phosphate buffer without compound serve as the controls. Dried discs are placed on the inoculated plates, four per plate, and the plates are incubated for 24 hours at 35° C. in a candle jar. Antibacterial activity is read in terms of the diameter of growth inhibition around the discs.

EXAMPLE 5

(*Neisseria gonorrhoeae* in vitro)

Antibacterial effects of polymers in terms of zones of growth inhibition of *Neisseria gonorrhoeae* was determined as described above. Results are shown in Table 6.

(2) Experimental compounds tested vs *Treponema pallidum.*

The test system consists of culture tubes containing *T. pallidum* broth with 0.5% w/v experimental compounds, inoculated with a 24 hr. broth culture of *T. pallidum,* and incubated for 48 hr. in an anaerobic atmosphere at 35° C. Control cultures of *T. pallidum* in broth without compound serve as the control. Anti-Treponemal activity is determined by adding 0.1 ml of a 1% triphenyltetrazolium solution to each culture at 48 hrs., re-incubating for 2 hrs., and reading tubes for color development (no anti-Treponemal effect) or lack of color (inhibition of growth and metabolism).

EXAMPLE 6

Anti-Treponemal activity of polymers as measured by inhibition of growth and metabolism was determined as described. Results are shown in Table 7.

TABLE 1

Protection against Herpes Simplex Virus, Type 1, in HEp-2 Monolayers, with Polymers.

| Polymer tested | Active Concentrations, Micrograms Polymer per ml. 50% plaque reduction |
|---|---|
| Blancol N[1] | 5 mcg. |
| Lomar D(3)[2] | 10 |
| Lomar LS[2] | 10 |
| Lomar PW(3)[2] | 5 |
| Lomar PWA[2] | 5 |
| Daxad 11G[3] | 10 |
| Daxad 11 KLS[4] | 5 |
| Darvan 1[5] | 5 |
| Darvan 2[6] | 25 |
| Harol 11[2] | 100–10 |
| Harol R6-71[8] | 1 |
| Daxad 11[3] | 10 |
| Daxad 13[3] | 5 |
| Daxad 15[3] | 5 |
| Daxad 19[9] | 10 |
| Daxad 21[10] | 100–50 |
| Daxad 23[11] | 1000–50 |
| Daxad 27[11] | 50 |
| Tamol N Micro[12] | 10 |
| Morwet D-425[13] | NOT ACTIVE |
| Alkanol XC[14] | 10 |

[1]Na salt of sulfonated naphthalene - HCHO condensate (GAF)
[2]Na salt of a condensed mononaphthalene sulfonic acid (NOPCO)
[3]Na salt of a polymerized alkylnaphthalene sulfonic acid (W. R. Grace)
[4]K salt of a polymerized alkylnaphthalene sulfonic acid (W. R. Grace)
[5]Na salt of naphthalenesulfonic acid - formaldehyde condensate (Vanderbilt).
[6]Na salt of polymerized substituted benzoid alkyl sulfonic acid (Vanderbilt).
[7]Na salt of polymerized substituted benzoid alkyl sulfonic acid (Garden Chemical and Equipment)
[8]Na salt of polymerized alkylnaphthalene sulfonic acid (Garden Chemical and Equipment)
[9]Na salt of highly polymerized alkyl naphthlene sulfonic acid (W. R. Grace)
[10]Mono-Ca salt of polymerized aryl alkyl sulfonic acid (W. R. Grace)
[11]Na salt of polymerized substituted benzoid alkyl sulfonic acid (W. R. Grace)
[12]Na salt of condensed naphthalene sulfonic acid (Rohm and Haas)
[13]Na salt naphthalene formaldehyde condensate (Petrochemicals Co.)
[14](F. I. DuPont Co.)

TABLE 2

Protection against Herpes Simplex Virus, Type 2, in HEp-2 Monolayers, with Polymers.

| Polymer tested | Active Concentrations, Micrograms Polymer per ml. 50% plaque reduction |
|---|---|
| Blancol N | 10–5 mcg. |
| Lomar D (3) | 25–5 |
| Lomar LS | 25–5 |
| Lomar PW(3) | 25–5 |
| Lomar PWA | 50–5 |
| Daxad 11G | 25–5 |
| Daxad 11 KLS | 25–5 |
| Darvan 1 | 50–5 |
| Darvan 2 | 100–10 |
| Harol 11 | 1000–250 |
| Daxad 11 | 10–5 |
| Harol R6-71 | 25–5 |
| Daxad 13 | 5 |
| Daxad 15 | 25–5 |
| Daxad 19 | NOT ACTIVE |
| Daxad 21 | 250–50 |
| Daxad 23 | 250–50 |
| Daxad 27 | 100–50 |
| Tamol N Micro | 10–1 |
| Morwet D-425 | 25 |
| Synthrapol DA-AC1 | 50 |
| Alkanol XC | 10 |

1.Na salt of napthalene sulfonic acid HCHO condensate (ICI Americas)

TABLE 3

Synergistic Activity of Polymers against Herpes Simplex Virus in HEp-2 Monolayers.

| Polymer | Activity (50% Plaque Reduction) Herpes Type I | Herpes Type II |
|---|---|---|
| Darvan 2 | 3–10 mcg/mL | 1–10 mcg/mL |
| Harol 11 | 30–1000 | 300–1000 |
| Daxad 11 | 10 | 10 |
| Daxad 13 | 5–15 | 5–15 |
| Tamol N Micro | 10 | 1–10 |
| Alkanol XC | 10 | 10 |
| Darvan 2 + Tamol N Micro | —* | — |
| Harol 11 + Tamol N Micro | 10 mcg + 1 mcg | — |
| Daxad 11 + Tamol N Micro | 3 mcg + 1 mcg | — |
| Daxad 13 + Tamol N Micro | — | — |
| Alkanol XC + Tamol N Micro | 3 mcg + 3 mcg | — |

*— activities not synergistic at levels tested.

TABLE 4

Treatment of Herpes Simplex Virus Infection in Guinea Pigs, Using Polymers.

| Polymer* | Mean Day of Disease Onset | Percent Protection |
|---|---|---|
| Type II Virus | | |
| Blancol N | Day 7 | 25% |
| Tamol SN | 9.25 | 50% |
| Lomar D | 9.25 | 50% |
| Lomar LS | 7 | 25% |
| Lomar PW(3) | 7.50 | 25% |
| Lomar PWA | 9.25 | 50% |
| Daxad 11 G | 4.25 | 0 |
| Daxad 11 KLS | 9.50 | 50% |
| Darvan 2 | 6.25 | 25% |
| Darvan 2 | 12.25 | 100% |
| Harol 11 | 12 | 75% |
| Harol R6-71 | 10 | 50% |
| Daxad 11 | 12.25 | 75% |
| Daxad 13 | 14 | 100% |
| Daxad 15 | 4.75 | 0 |
| Daxad 21 | 6.75 | 25% |
| Daxad 23 | 12.25 | 50% |
|  | 12.25 | 75% |
| Tamol N Micro | 14 | 100% |
|  | 9.75 | 50% |
|  | 14 | 100% |
| Control (vehicle) | 2.5 | 0 |
|  | 3.75 | 0 |
|  | 4 | 0 |
|  | 4.25 | 25% |
|  | 5 | 0 |
| Type I Virus | | |
| Daxad 13 | Day 10 | 50% |
| Daxad 23 | 12.75 | 100% |
| Tamol N Micro | 14 | 100% |
|  | 10.5 | 75% |
| Control (vehicle) | 3 | 50% |
|  | 3.8 | 25% |
|  | 6.75 | 50% |

*Compounds were used as a 5% w/v suspension in pH 7.2 phosphate buffer. Animals were dosed intravaginally 30 minutes pre-infection, 30 minutes and 4 hours post-infection, and thrice daily for the following four days.

TABLE 5

Treatment of Herpes Simplex Virus Type I Infection in Guinea Pigs. Using Single Polymers and Concentrations of these.

| Polymer | Mean Day of Disease Onset | Percent Protection |
|---|---|---|
| Harol 11 5% | Day 10.9 | 44% |

TABLE 5-continued

Treatment of Herpes Simplex Virus Type I Infection in Guinea Pigs. Using Single Polymers and Concentrations of these.

| | Results | |
|---|---|---|
| Polymer | Mean Day of Disease Onset | Percent Protection |
| Daxad 11 5% | 11.7 | 70% |
| Tamol N Micro 5% | 10.9 | 63% |
| Harol 11/Tamol N Micro 5% each | 11.8 | 70% |
| Daxad 11/Tamol N Micro 5% each | 11.9 | 70% |
| Buffer control | 7.8 | 30% |
| Lomar PWA 10% | Day 9.6 | 70% |
| Daxad 11 10% | 8.7 | 44% |
| Lomar/Tamol N Micro 5% ea. | 8.0 | 10% |
| Daxad 11/Tamol N Micro 5% ea. | 10.4 | 67% |
| Tamol N Micro/Alkanol XC 5% ea. | 11.5 | 90% |
| Buffer control | 7.2 | 30% |

TABLE 6

Antibacterial Effect of Polymers on *Neisseria Gonorrhoeae*

| Polymer Tested | Inhibition of Growth, mm |
|---|---|
| Blancol N | 13.4 mm |
| Lomar D | 13.5 |
| Lomar LS | 14.1 |
| Lomar PW(3) | 15.3 |
| Daxad 11G | 14.4 |
| Daxad 11 KLS | 16.1 |
| Darvan 2 | 0 no inhibition |
| Daxad 23 | 0 no inhibition |
| Tamnol N Micro | 15.7 |

TABLE 7

Anti-treponemal Effect of Polymers Tested as *Treponema pallidum*.

| Polymer Tested | Inhibition of Treponema (+) |
|---|---|
| Blancol N | + |
| Lomar D | + |
| Lomar LS | + |
| Lomar PW(3) | + |
| Daxad 11G | + |
| Daxad 11 KLS | + |
| Darvan 2 | − |
| Daxad 23 | − |
| Tamol N Micro | + |

FORMULATION AND ADMINISTRATION

Effective quantities of antiviral arylsulfonic acid polymers may be administered topically to the tissue of a living animal body under attack by the *Herpes simplex* virus in any one of various ways depending on the site of infection. When the oral cavity is involved, liquid preparations to be used as mouthwashes, swabs, or lipsticks are ideal vehicles for carrying arylsulfonic and polymers. Such suitable liquid prepartions may contain 0.5 to 20.0% arylsulfonic acid polymers. When the genital area is involved, powders, solutions, emulsions, jellies, ointments, and suppositories may be used within these same concentration ranges. Ideally, the tissues under attack are treated 2–4 times daily.

The active agents of the invention may be combined with other pharmacologically active agents, buffers, and antacids or the like for administration.

Examples of compositions within the ranges given are as follows and are representative for all of the pharmacologically active arylsulfonic acid polymers of the invention but have been especially designed to embody as active ingredient the arylsulfonic acid polymers which have been purified as described hereinabove.

MOUTH WASH

| | Solution Formulations Percent Arylsulfonic Acid Polymers | |
|---|---|---|
| Ingredients | 5% | 10% |
| 1. Arylsulfonic Acid Polymers | 50.0 gm. | 100.0 gm. |
| 2. Sarbo | 150.0 ml. | 150.0 ml. |
| 3. Glycerin | 100.0 ml. | 100.0 ml. |
| 4. Sodium Benzoate | 1.0 gm. | 1.0 gm. |
| 5. Sucrose | 40.0 gm. | 50.0 gm. |
| 6. Peppermint Flavor Compound No. 21444 Fritzsche | 0.35 ml. | 0.75 ml. |
| 7. Oil of Spearmint N.F. Fritzsche | 0.5 ml. | 0.75 ml. |
| 8. Alcohol, U.S.P. 95% | 50.0 | 50.0 ml. |
| 9. Caramel Color Acid-proof | 6.0 | — |
| 10. Water U.S.P., q.s. | 1000.0 ml. | 1000.0 ml. |

PROCEDURE

1. Dissolve the sodium benzoate in 350 ml. of water.
2. Mix arylsulfonic acid polymers and sucrose and add this to the mixing solution from step No. 1.
3. After step No. 2 is a solution, add the glycerin and sorbo.
4. Put the flavors in part of the alcohol and add this to the solution. Rinse the container with the remainder of the alcohol and add to batch.
5. Add caramel.
6. Q.S. to final volume with water.

VAGINAL SUPPOSITORIES

| | | Formulations, Percent Arylsulfonic Acid Polymers | |
|---|---|---|---|
| | Ingredients | 5% | 10% |
| 1. | Arylsulfonic acid polymers | 100 mg. | 200 mg. |
| 2. | Polyethylene glycol 1000 | 1420 | 1350 mg. |
| 3. | Polyethylene glycol 4000 | 480 | 450 mg. |

PROCEDURE

1. Melt 2 and 3 together and stir until uniform.
2. Stir arylsulfonic acid polymers in the molten mass from step 1 until uniform.
3. Pour the molten mass from step 2 into suppository mold and chill.
4. Remove the suppository from the mold and wrap.

VAGINAL DOUCHE

| | Ingredients | 2.0% | 5% | 10% |
|---|---|---|---|---|
| 1. | Arylsulfonic acid polymers | 20.0 gm. | 50.0 gm. | 100.0 gm. |
| 2. | Liquefied phenol | 5. cc | 5. cc | 5 cc |
| 3. | Glycerin | 125 cc | 125 cc | 125 cc |
| 4. | Water, U.S.P., q.s. | 1000 ml. | 1000 ml. | 1000 ml. |

PROCEDURE

1. Dissolve the arylsulfonic acid polymers in 500 cc distilled water.
2. Mix phenol and glycerin and add to (1).
3. Q.S. to final volume with water.

| DOUCHE POWDER | | |
|---|---|---|
| 1. | Sodium Borate | 575 g. |
| 2. | Arylsulfonic Acid Polymers | 400 g. |
| 3. | Phenol | 5 g. |
| 4. | Thymol | 5 g. |
| 5. | Menthol | 5 g. |
| 6. | Eucalyptol | 5 cc. |
| 7. | Methyl salicylate | 5 cc. |

Mix intimately and pass through a No. 60 sieve.

To prepare a 2% arylsulfonic acid polymer douche, mix 50 grams of the powder to 950 ml. distilled water.

Various modifications and equivalents will be apparent to one skilled in the art and may be made in preparing the arylsulfonic acid polymers, in the compositions and in the methods of the present invention without departing from the spirit or scope thereof, and it is therefrom understood that the invention is to be limited only by the scope of the appended claims.

We claim:

1. A method of treating viral infections caused by Type I or Type II *Herpes simplex* viruses comprising topically administering to infected tissue of a living animal under attack by said virus an effective amount of an arylsulfonic acid polymer having a repeating unit selected from the group consisting of the following structures:

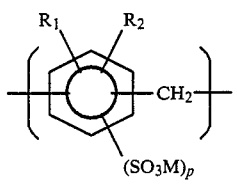

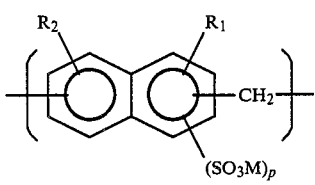

wherein $R_1$ and $R_2$ are selected from the group consisting of hydrogen, alkyl having 1 to 20 carbon atoms, alkoxy having 1 to 20 carbon atoms, fluorine, chlorine and bromine; $R_3$ is hydrogen, alkoxy having 1 to 20 carbon atoms; X is selected from the group consisting of a direct covalent bond between the aromatic rings, a loweralkylene having 1 to 5 carbon atoms, a lower alkylene having 2 to 5 carbon atoms, oxygen, sulfur, and $-O(CH_2)_nO-$ wherein n is an integer from 2 to 20; p is from about 0.4 to about 1.2; the sum of q and r is from about 0.8 to about 2.4; and M is selected from the group consisting of lithium, sodium, potassium, calcium, magnesium, zinc, aluminum, hydrogen, ammonium and substituted ammonium ions derived from pharmaceutically acceptable organic amines.

2. The method of claim 1 wherein said arylsulfonic acid polymer is a condensation polymer of an arylsulfonic acid with formaldehyde.

3. The method according to claim 2 wherein said arylsulfonic acid is naphthelene sulfonic acid.

4. The method according to claim 3 wherein said sulfonic acid groups are in the form of a sodium or zinc salt.

5. The method of claim 1 wherein said viral infection causes venereal disease in humans.

* * * * *